United States Patent [19]

Nestor et al.

[11] 4,256,737
[45] Mar. 17, 1981

[54] LONG ACTING DEPOT INJECTABLE FORMULATIONS FOR LH-RH ANALOGUES

[75] Inventors: John J. Nestor, San Jose; Brian H. Vickery, Cupertino, both of Calif.

[73] Assignee: Syntex (U.S.A.) Inc., Palo Alto, Calif.

[21] Appl. No.: 47,662

[22] Filed: Jun. 11, 1979

[51] Int. Cl.³ .............. A61K 37/02; A61K 37/24; A61K 37/38
[52] U.S. Cl. .................................................. 424/177
[58] Field of Search .............. 260/112.5 LH; 424/177

[56] References Cited

U.S. PATENT DOCUMENTS

| 3,149,036 | 9/1964 | Woodhur et al. | 424/88 |
| 3,855,199 | 12/1974 | Foell et al. | 424/177 |
| 3,886,135 | 5/1975 | McKinley et al. | 424/177 |
| 3,892,723 | 7/1975 | McKinley et al. | 424/177 |
| 3,915,947 | 10/1975 | Shields | 424/177 |
| 3,928,307 | 12/1975 | Foell et al. | 424/177 |
| 3,928,308 | 12/1975 | Yardley | 424/177 |
| 3,992,365 | 11/1976 | Beddell et al. | 424/177 |
| 4,003,884 | 1/1977 | König et al. | 424/177 |
| 4,008,209 | 2/1977 | Fujino et al. | 424/177 |
| 4,010,125 | 3/1977 | Schally et al. | 260/112.5 LH |
| 4,010,149 | 3/1977 | Baba et al. | 424/177 |
| 4,072,668 | 2/1978 | Amoss et al. | 424/177 |
| 4,075,191 | 2/1978 | Beddell et al. | 424/177 |
| 4,118,483 | 10/1978 | König et al. | 424/177 |
| 4,124,703 | 11/1978 | Dutta et al. | 424/177 |
| 4,128,638 | 12/1978 | Moody | 424/177 |
| 4,143,133 | 3/1979 | Foell et al. | 424/177 |

OTHER PUBLICATIONS

Biological Abst., vol. 63, pp. 25180, 25181, 1977.
Rivier, et al., Endocrinology 103, 2299–2305, 1978.

Primary Examiner—Delbert R. Phillips
Attorney, Agent, or Firm—Alan M. Krubiner; Tom M. Moran

[57] ABSTRACT

The biological activity of super agonist analogues of LH-RH is extended for long periods of time by incorporation of such analogues in a vehicle comprising an oil of vegetable origin and a gelling agent, preferably an aluminum mono-fatty acid ester. Pharmaceutical compositions thus formed are suitable for depot injection.

1 Claim, No Drawings

LONG ACTING DEPOT INJECTABLE FORMULATIONS FOR LH-RH ANALOGUES

BACKGROUND OF THE INVENTION

In recent years a series of highly active analogues of the natural releasing hormone LH-RH have been prepared. These compounds are referred to as super agonists and exhibit so called "paradoxical" high dose effects, for example, blockage of ovulation in the female, suppression of spermatogenesis in the male, and suppression of normal circulating levels of sexual steroids of gonadal origin, including reduction in accessory organ weight in the male and female. In general these compounds can be used for contraception in the male and female, for reduction of accessory organ weight (e.g. prostate size in the male) and so forth.

The natural LH-RH has a peptide sequence as follows: (pyro)Glu-His-Trp-Ser-Tyr-Gly-Leu-Arg-Pro-Gly-NH$_2$. The conventional abbreviations for the various common amino acids are used as generally accepted in the peptide art as recommended by the IUPAC-IUB Commission on Biological Nomenclature. The N-terminal amino acid is written on the left and the C-terminal amino acid on the right. The most significant chemical modification of the basic natural LH-RH molecule leading to increased activity has been obtained by changing the 6-position amino acid residue from glycine to a D-amino acid. Particularly active analogues are those where the Gly residue in the 6-position is replaced by D-Phe, D-Trp, D-Leu, D-Ala or D-Ser(t-Bu).

In addition, further increases in activity have been obtained by replacing the Gly-NH$_2$ terminus by a Pro-NHR terminus, where R is, for example, lower alkyl (preferably ethyl), cycloalkyl, fluoroalkyl or

("Aza-Gly"-NHR$^1$) where R$^1$ is hydrogen or lower alkyl. Coupling of this modification with the aforementioned modification in the 6-position leads to highly active compounds.

Especially active LH-RH super agonists heretofore described are:
[D-Phe$^6$]LHRH, [D-Trp$^6$]LHRH, [D-Leu$^6$]LHRH, [D-Ala$^6$]LHRH, desGly$^{10}$-[D-Phe$^6$, ProNHEt$^9$]LHRH, desGly$^{10}$-[D-Trp$^6$, ProNHEt$^9$]LHRH, desGly$^{10}$-[D-Ala$^6$, ProNHEt$^9$]LHRH, desGly$^{10}$-[D-Leu$^6$, ProNHEt$^9$]LHRH, desGly$^{10}$-[D-Ser(t-Bu)$^6$, ProNHEt$^9$]LHRH and desGly$^{10}$-[D-Ser(t-Bu)$^6$, Aza-Gly-NH$_2$$^{10}$]LHRH. The nomenclature is that generally accepted in the LH-RH art, wherein the nature and position of modifications to the natural LH-RH are shown before and within the brackets.

While these compounds are highly active and exhibit a relatively long biological halflife (e.g. 8–10 hours) in comparison to the natural LH-RH (1–2 hours), it would be desirable to have available pharmaceutical compositions for depot injectable use that could provide, in a single administration, release of effective amounts of the LH-RH analogue over periods of from 1 week to as much as 1 year.

The use of complexing agents such as tannic acid, and gelling agents such as aluminum monostearate to control drug solubility and the rate of drug transfer, respectively, is generally known. See, for example, "Sustained and Controlled Release Drug Delivery Systems", J. R. Robinson, Ed, Marcel Dekker, Inc. New York, 1978, pp. 178 and 189.

DESCRIPTION OF THE INVENTION

The present invention relates to novel pharmaceutical compositions for LH-RH analogues. More particularly the present invention relates to long acting pharmaceutical compositions suitable for depot injectable use comprising an LH-RH super-agonist analogue in admixture with a vehicle comprising an oil of vegetable origin and a gelling agent. These compositions may be used for any of the so-called "paradoxical" high-dose uses known for LH-RH analogues, e.g. male or female contraception, reduction of accessory organ weight, and the like.

Particularly preferred LH-RH super agonist analogues are those described above in the "Background of the Invention" as well as others described in the literature. In particular, these include compounds wherein the Gly residue in the 6-position is replaced by a D-amino acid, most preferably D-Ala, D-Leu, D-Phe, D-Trp or D-Ser(t-Bu) and, optionally wherein the C-terminus is ProNHR wherein R is lower alkyl, cycloalkyl, fluoroalkyl or

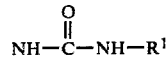

where R$^1$ is hydrogen or lower alkyl. "Lower alkyl" as used herein refers to straight or branched chain alkyl of 1-4 carbon atoms.

In addition, the LH-RH analogues may be present as "pharmaceutically acceptable salts." Such term refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid, and the like; (b) salts with polyvalent metal cations such as zinc, calcium, bismuth, barium, magnesium, aluminum, copper, cobalt, nickel, cadmium, and the like; or with an organic cation formed from, N, N'-dibenzylethylenediamine or ethylenediamine; or (c) combinations, of (a) and (b), e.g. a zinc tannate salt, and the like.

In one aspect of the present invention a relatively water soluble salt (primarily a salt with a monovalent acid, e.g., an acetate) of the LH-RH analogue is incorporated into the pharmaceutical composition.

In another aspect of the present invention an exceptionally long duration of action of the LH-RH analogue is obtained by incorporating a salt which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acid, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt.

Particularly preferred salts are zinc salts, zinc tannate salts, pamoate salts, and the like.

As vehicle for the pharmaceutical composition there is utilized an oil of vegetable origin in combination with a gelling agent.

As typical oils of vegetable origin there may be mentioned sesame oil, peanut oil, corn oil, safflower oil, olive oil, and the like.

As gelling agents there may be mentioned, in particular aluminum mono-fatty acid esters, for example, aluminum monostearate, aluminum mono-oleate, aluminum monolaurate, aluminum monomyristate, aluminum monopalmitate, and the like.

A particularly preferred vehicle comprises sesame oil in combination with aluminum monostearate.

The gelling agent, e.g. aluminum monostearate, is preferably present in an amount between about 0.5 and 10.0% by weight relative to the oil of vegetable origin, preferably between about 1 and 3% by weight, most preferably about 2% by weight.

The LH-RH analogue is present in an effective amount for the desired end result, usually in an amount between about 0.01% and 1% by weight relative to the vehicle, preferably about 0.1% by weight relative to the vehicle.

The pharmaceutical compositions of the present invention may conveniently be prepared by any of the methods well-known in the pharmaceutical art, for example, as described in Remmington's Pharmaceutical Sciences, Mack Publishing Co., Easton, PA, 1970. For example, one method of preparation of the pharmaceutical compositions of the present invention involves combining the gelling agent and the oil of vegetable origin, heating to form a solution, cooling and adding the LH-RH analogue.

The pharmaceutical compositions of the present invention are conveniently administered to the subject by injection, for example, subcutaneously or intramuscularly, in a depot form. The LH-RH analogue, or salt thereof, is slowly released into the body circulation over prolonged periods of time, for example, from 1 week to 1 year from a single administration. These results are indeed surprising in comparison with the administration of the same compound, or even an insoluble salt, in for example, the oil of vegetable origin alone.

The invention is further illustrated and explained by reference to the following examples. These examples should not be construed as a limitation upon the scope of the invention, but merely as being illustrative and representative thereof.

EXAMPLE 1

A. Preparation of zinc tannate salt of desGly$^{10}$-[D-Trp$^6$, ProNHEt]LHRH$^9$-

To a solution of 7.55 mg of tannic acid in 0.08 mL of 0.25 M NaOH was added sequentially a solution of 10.3 mg of desGly$^{10}$-[D-Trp$^6$, ProNHEt$^9$]LHRH acetate salt in 0.1 mL of Water and a solution of 4.6 mg of zinc sulfate heptahydrate in 0.1 mL water. The resulting precipitate was allowed to stand for 2 hours at 25° C. and was spun down in a centrifuge tube. The supernatant was decanted and the precipitate was washed with 0.8 mL of water by centrifugation and decantation of the supernatant. The precipitate was dried in vacuo to yield 14.9 mg of the mixed zinc tannate salt of desGly$^{10}$-[D-Trp$^6$, ProNHEt$^9$]-LHRH was a grey powder.

B. Zinc salt of desGly$^{10}$-[D-Trp$^6$,ProNHEt$^9$]LHRH

To a solution of 13 mg desGly$^{10}$-[D-Trp$^6$,ProNHE$^9$]-LHRH acetate salt in a mixture of 0.075 mL water and 0.08 mL of 0.25 M sodium hydroxide was added a solution of 4.6 mg of zinc sulfate heptahydrate in 0.075 mL of water. The precipitate was centrifuged and the supernatant was decanted. The precipitate was washed with 1 mL of water. The precipitate was again centrifuged, the supernatant was decanted and the precipitate was dried in vacuo to yield 7.3 mg of the zinc salt of the above-named LH-RH analogue as a grey powder.

C. Pamoate salt of desGly$^{10}$-[D-Trp$^6$, ProNHEt$^9$]-LHRH-

To a solution of 10.9 mg of desGly$^{10}$-[D-Trp$^6$, ProNHEt$^9$]LHRH acetate salt in 0.075 mL of water was added a solution of 2.3 mg of pamoic acid in 0.08 mL of 0.25 M NaOH. The precipitate which formed was spun down and the supernatant was decanted. The precipitate was washed with 1 mL water, spun down, and the supernatant was decanted. The precipitate was dried in vacuo to yield 7.43 mg of the pamoate salt of the above-named LH-RH analogue as a light yellow powder.

EXAMPLE 2

| Preferred fprmulation | |
|---|---|
| LH-RH analogue | 1.0 mg |
| aluminum monostearate, USP | 20.0 mg |
| sesame oil q.s. ad | 1.0 ml |

The aluminum monostearate is combined with the sesame oil and heated to 125° C. with stirring until a clear yellow solution forms. This mixture is then autoclaved for sterility and allowed to cool. The LH-RH analogue is then added aseptically with trituration. Typical LH-RH analogues that may be used are those whose preparation is described in Example 1.

EXAMPLE 3

This example describes the exceptionally long duration of action obtained with typical LH-RH analogues in the pharmaceutical compositions of the present invention. Biological activity was measured by following estrus suppression in the rat resulting from a single subcutaneous administration of the composition. The experiment was carried out as follows:

Sprague-Dawley rats (180–190 grams) were individually weighed and grouped. A vaginal smear was taken and the animals were then injected with 1 ml each of vehicle or test composition subcutaneously. Daily vaginal smears were taken until the rats returned to normal estrus cycling.

The first group received 1 ml of vehicle alone per rat. The vehicle consisted of 2% aluminum monostearate in sesame oil.

The second group received 1 ml per rat of the above-described vehicle containing 1 mg/ml of desGly$^{10}$-[D-Trp$^6$, ProNHEt$^9$]LHRH as its acetate salt.

The third group received 1 ml per rat of the above-described vehicle containing 2 mg/ml (equivalent to 1 mg/ml of LH-RH base analogue) of the zinc tannate salt of desGly$^{10}$-[D-Trp$^6$, ProNHEt$^9$]LHRH.

The average number of days from administration at which 50% of the rats in the group showed return of estrus was as follows:
vehicle alone—1-2 days,
LH-RH analogue as acetate salt—38 days,
LH-RH analgoue as zinc tannate salt—120 days.

Utilization of, for example, the zinc salt or the pamoate salt affords comparable results.

Use of the above-described salts in a standard sesame oil preparation without a gelling agent results in return of estrus for 50% of the population in approximately 7-14 days.

Similar results may be obtained utilizing other LH-RH analogues and their salts.

What is claimed is:

1. A pharmaceutical composition for release of an analogue of luetinizing hormone-releasing hormone or a pharmaceutically acceptable salt thereof over an extended period of time comprising between about 0.01 and 1.0 percent by weight of a pharmaceutically acceptable salt of said analogue, said salt selected from the group consisting of the zinc, zinc tannate and pamoate salts of

[D-Phe$^6$]LHRH, [D-Trp$^6$]LHRH, [D-Leu$^6$]LHRH, [D-Ala$^6$]LHRH, desGly$^{10}$-[D-Phe$^6$, ProNHEt$^9$]LHRH, desGly$^{10}$-[D-Trp$^6$, ProNHEt$^9$]LHRH, desGly$^{10}$-[D-Ala$^6$, ProNHEt$^9$]LHRH, desGly$^{10}$-[D-Leu$^6$, ProNHEt$^9$]LHRH, desGly$^{10}$-[D-Ser(t-Bu)$^6$, ProNHEt$^9$]LHRH and desGly$^{10}$-[D-Ser(t-Bu)$^6$, Aza-Gly-NH$_2$$^{10}$]LHRH in admixture with a vehicle comprising (i) between about 1-3% by weight of aluminum monostearate and (ii) an oil of vegetable origin.

* * * * *